United States Patent

Nara

Patent Number: 5,276,297
Date of Patent: Jan. 4, 1994

[54] MELTING DISPOSAL APPARATUS FOR INJECTION NEEDLES

[75] Inventor: Akikazu Nara, Kyoto, Japan

[73] Assignee: Naraseiki Kabushiki Kaisha, Kyoto, Japan

[21] Appl. No.: 743,176

[22] Filed: Aug. 9, 1991

[30] Foreign Application Priority Data

Sep. 18, 1990 [JP] Japan .................. 2-248376

[51] Int. Cl.$^5$ .............................. B23K 9/00
[52] U.S. Cl. ..................... 219/121.43; 219/68; 219/121.37; 422/21; 422/22; 422/906
[58] Field of Search ............ 219/121.4, 121.43, 68, 219/121.37, 121.38; 422/292, 21–; 250/491.1, 492.1, 424

[56] References Cited

U.S. PATENT DOCUMENTS

| | | | |
|---|---|---|---|
| 4,423,303 | 12/1983 | Hirose et al. | 219/121.43 |
| 4,900,894 | 2/1990 | Tanaka et al. | 219/121.38 |
| 4,931,261 | 6/1990 | Jacob | 250/424 |

FOREIGN PATENT DOCUMENTS 0223964  9/1989  Japan .................. 219/69.1

Primary Examiner—Mark H. Paschall
Attorney, Agent, or Firm—Leydig, Voit & Mayer

[57] ABSTRACT

A melting disposal apparatus for injection needles having a unit for generating electromagnetic microwave, unit for generating a plasma discharge with high temperature by being irradiated with the electromagnetic microwave, and moving unit for automatically inserting the injection needle into the zone in which said plasma discharge is produced, and automatically releasing the injection needle from the zone after the injection needle has been molten.

8 Claims, 6 Drawing Sheets

MELTING DISPOSAL APPARATUS FOR INJECTION NEEDLES

BACKGROUND OF THE INVENTION

The present invention relates to an apparatus in which injection needles are melted through high temperature thereby safely and easily disposing them.

Hitherto, the injection needle used in hospital or the like has been inevitably disposed in a specific root that the injection needles are collected in a predetermined vessel with sufficient carefulness so as not to inject fingers of person or the like. Therefore, it is necessary to treat the used injection needle very carefully so as to produce bacterial infection.

SUMMARY OF THE INVENTION

The object of the present invention is to solve the problems of the conventional technique and is to present a melting disposal apparatus for injection needles, featured in the construction characterized in that means for generating electromagnetic microwave, means for generating a plasma discharge with high temperature by being irradiated with said electromagnetic microwave, and moving means for automatically inserting said injection needle into the zone in which said plasma discharge is produced, and automatically releasing said injection needle from said zone after said injection needle has been melted.

DESCRIPTION OF THE PREFERRED EMBODIMENT

One embodiment of the present invention will be explained with reference to the attached drawings hereinafter.

Figure 1:
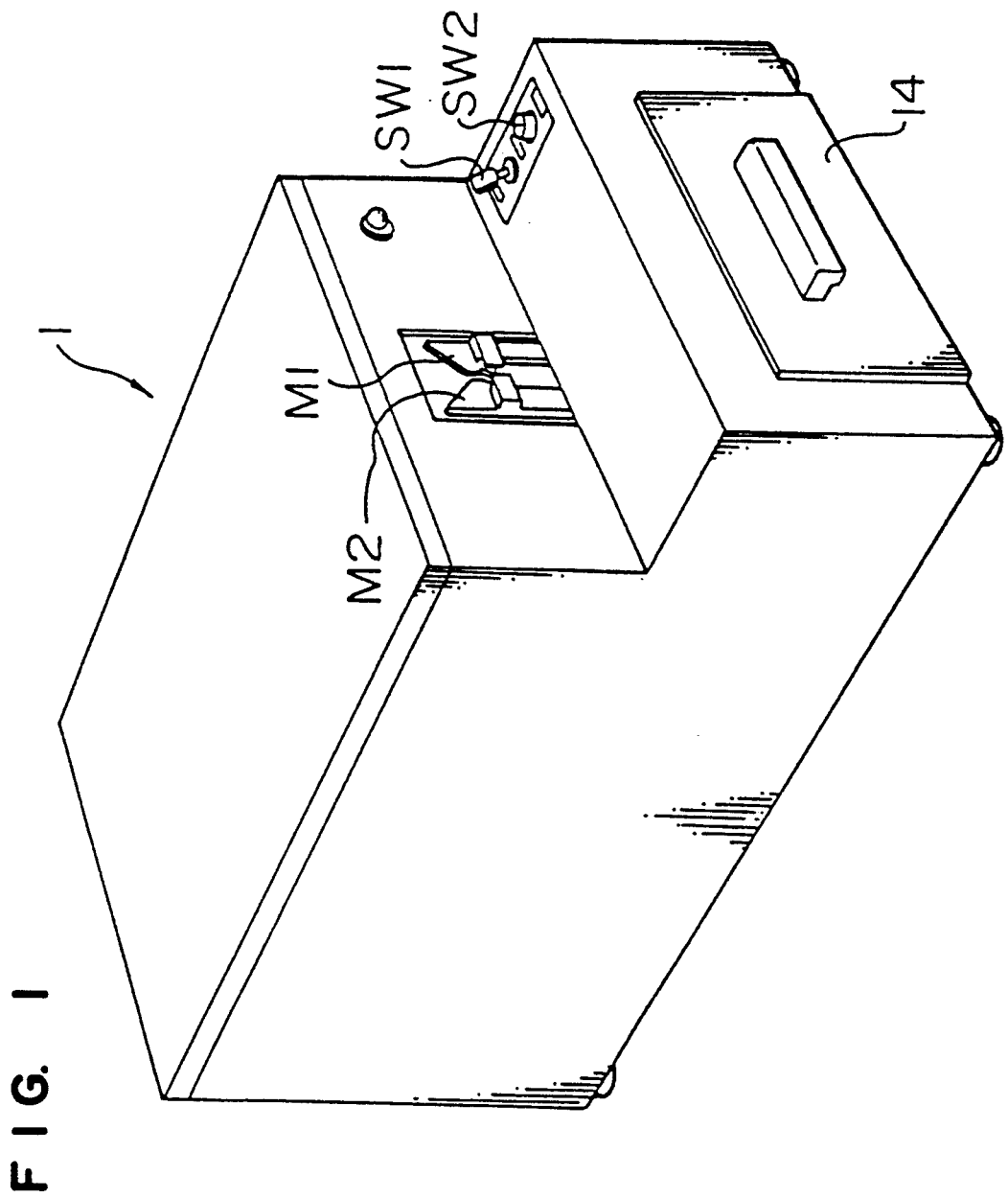
FIG. 1 is a perspective view showing the injection needle melting apparatus as one embodiment of the present invention.
Figure 2:
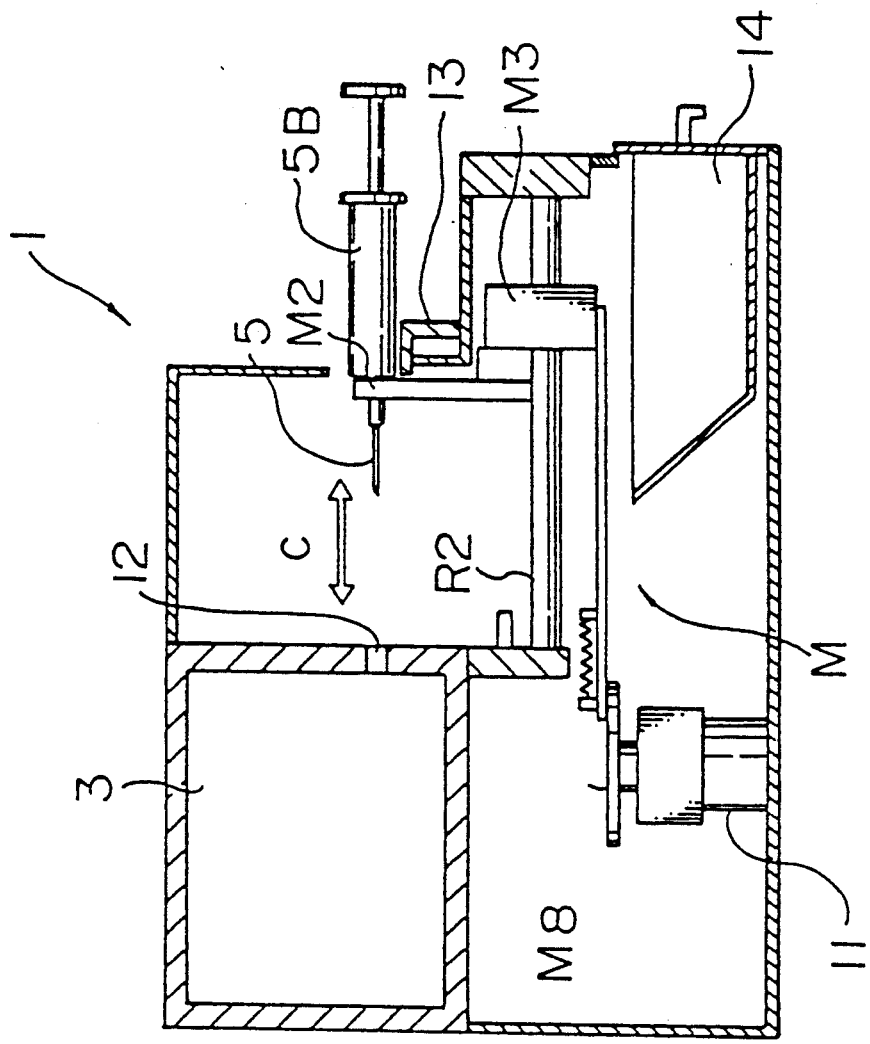
FIGS. 2 and 3 are schematic side sectional and perspective views respectively showing the interior constructions.
Figure 3:
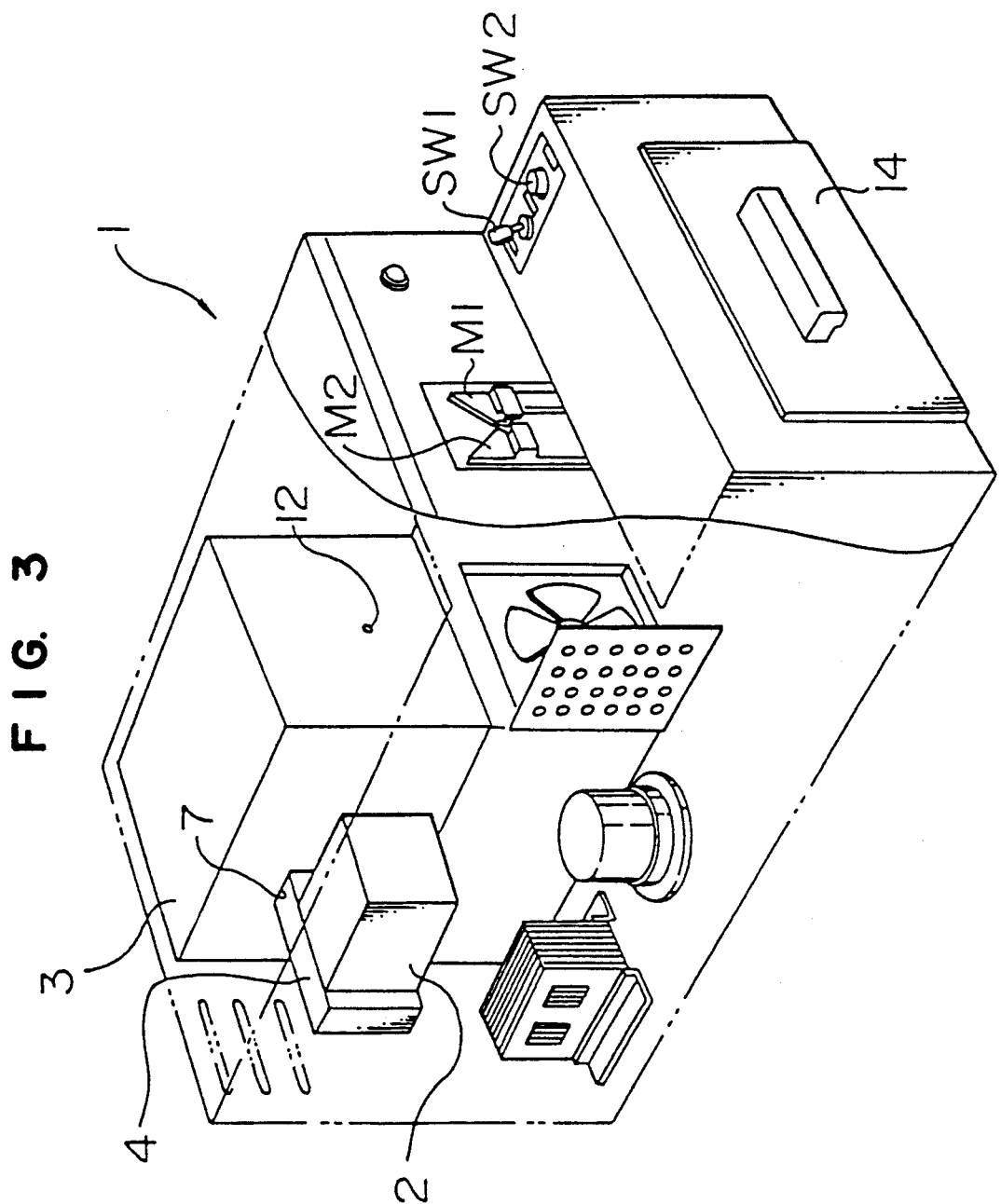

FIG. 1 shows an injection needle melting disposal apparatus. FIGS. 2 and 3 show a schematic construction of the apparatus in which a microwave generator 2 (100 volt, 500 wattage) for generating an electromagnetic microwave (about 2450 KHz) is disposed on the side wall of a melting furnace 3 through a waveguide tube 4. There is provided moving means M for automatically inserting an injection needle 5 into the melting furnace 3 and automatically returning it after melting thereof.

In the interior of a melting furnace 3 made of stainless steel or the like, there is provided two tungsten wires W1 and W2 fixed on a supporting plate, one end point of each of two wires is disposed in adjacent to each other (with a gap between end points of about 2 mm).

Figure 4:
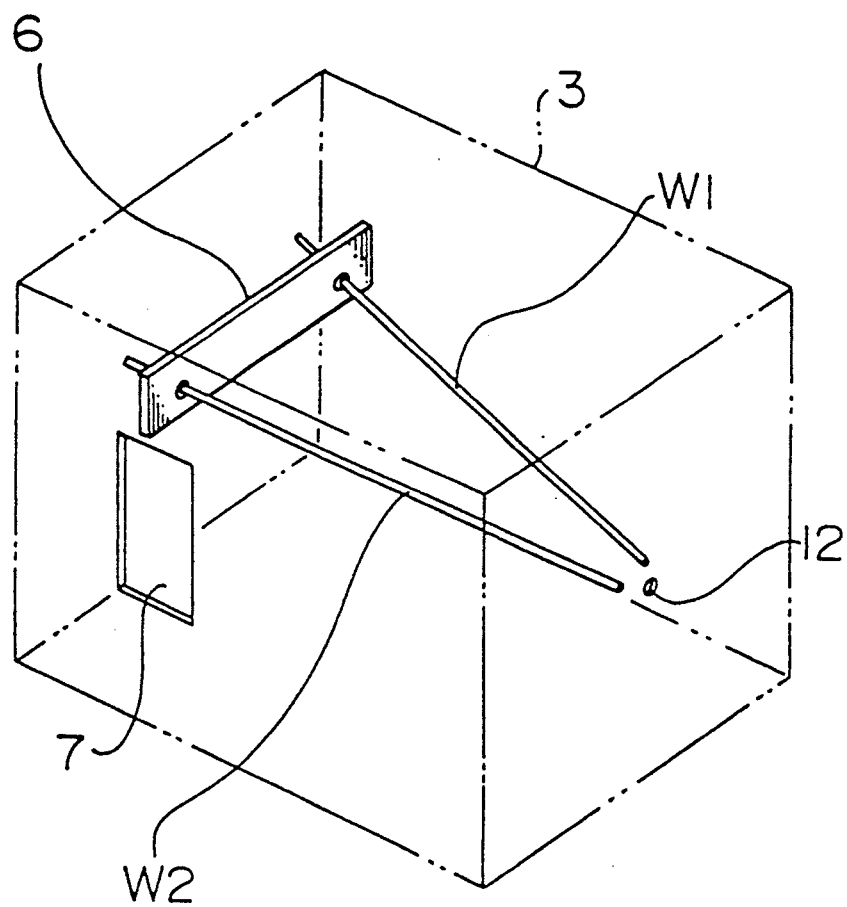
FIG. 4 is a schematic and perspective view showing the interior of the melting furnace.

An opening 7 in FIG. 4 is provided on the side surface of the melting furnace made of stainless steel for the waveguide tube 4, and the electromagnet microwave is irradiated from the opening 7 into the tungsten wires W1 and W2 (having diameter about 1.6 mm) mounted within the melting furnace 3.

Figure 5:
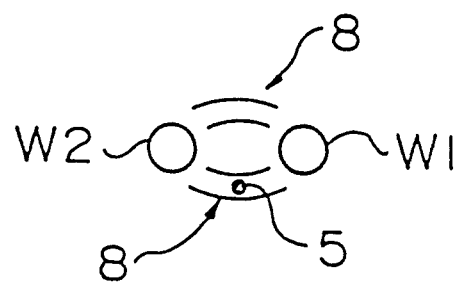
FIG. 5 is a front view showing the end points of tungsten wires.

Upon the irradiation of the electromagnetic microwave, a plasma discharge 8 is produced at the zone between the end points of the tungsten wires W1 and W2 respectively as shown in FIG. 5, and a high temperature about 4000° C.-5000° C. is produced. The injection needle 5 is disposed in the plasma discharge 8. The time required for disposing one injection needle 5 is about 5-10 seconds. The electromagnetic microwave is generated only during the time corresponding the above-mentioned disposal time. The end point of the tungsten wire is gradually worn thereby increasing the distance between the end points, and therefore the tungsten wire is adjustably mounted on a supporting plate 6 so as to be pulled slightly.

Figure 6:
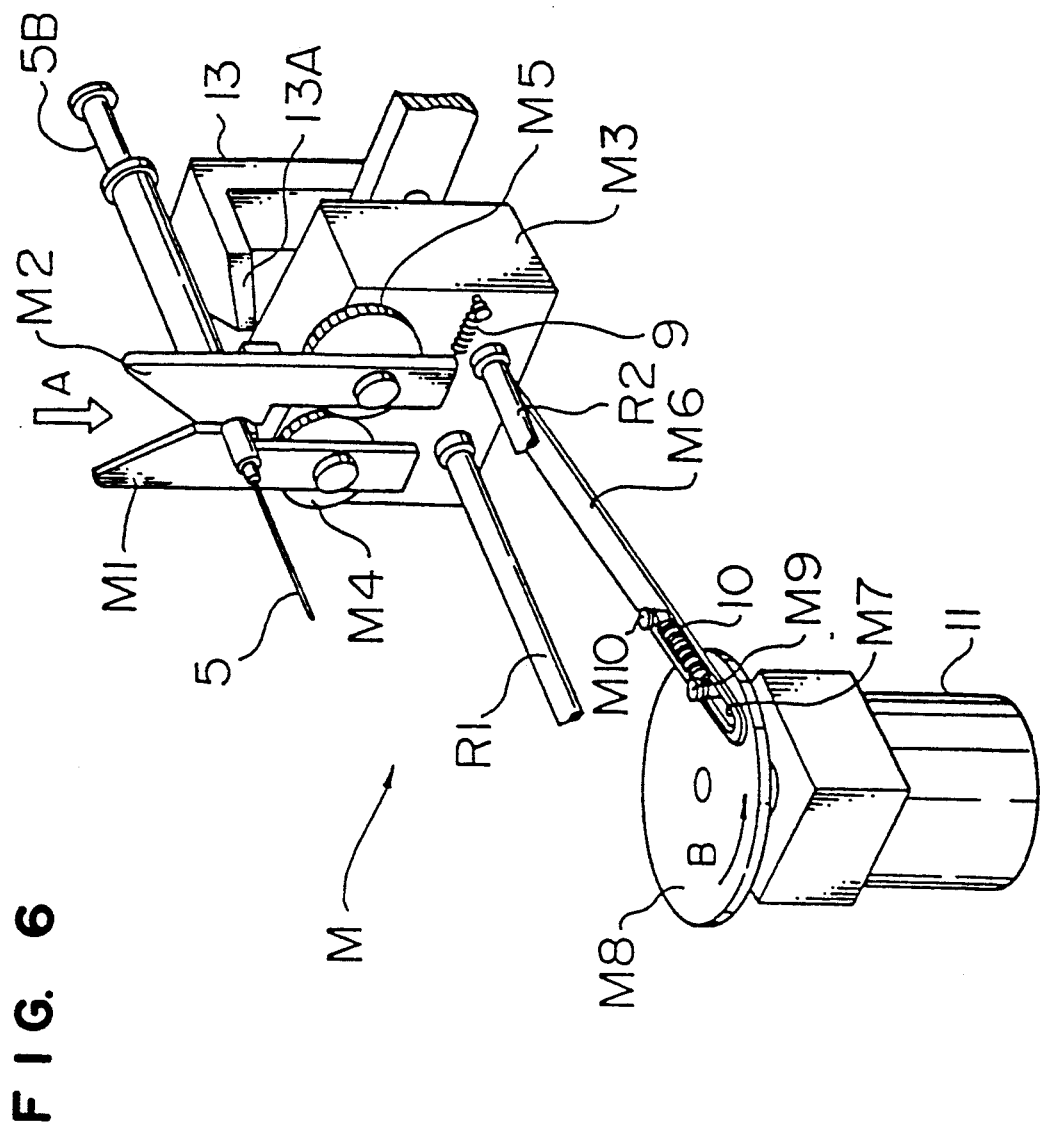
FIGS. 6 and 7 are schematic and perspective views respectively showing the construction of moving means for automatically moving the injection needle.
Figure 7:
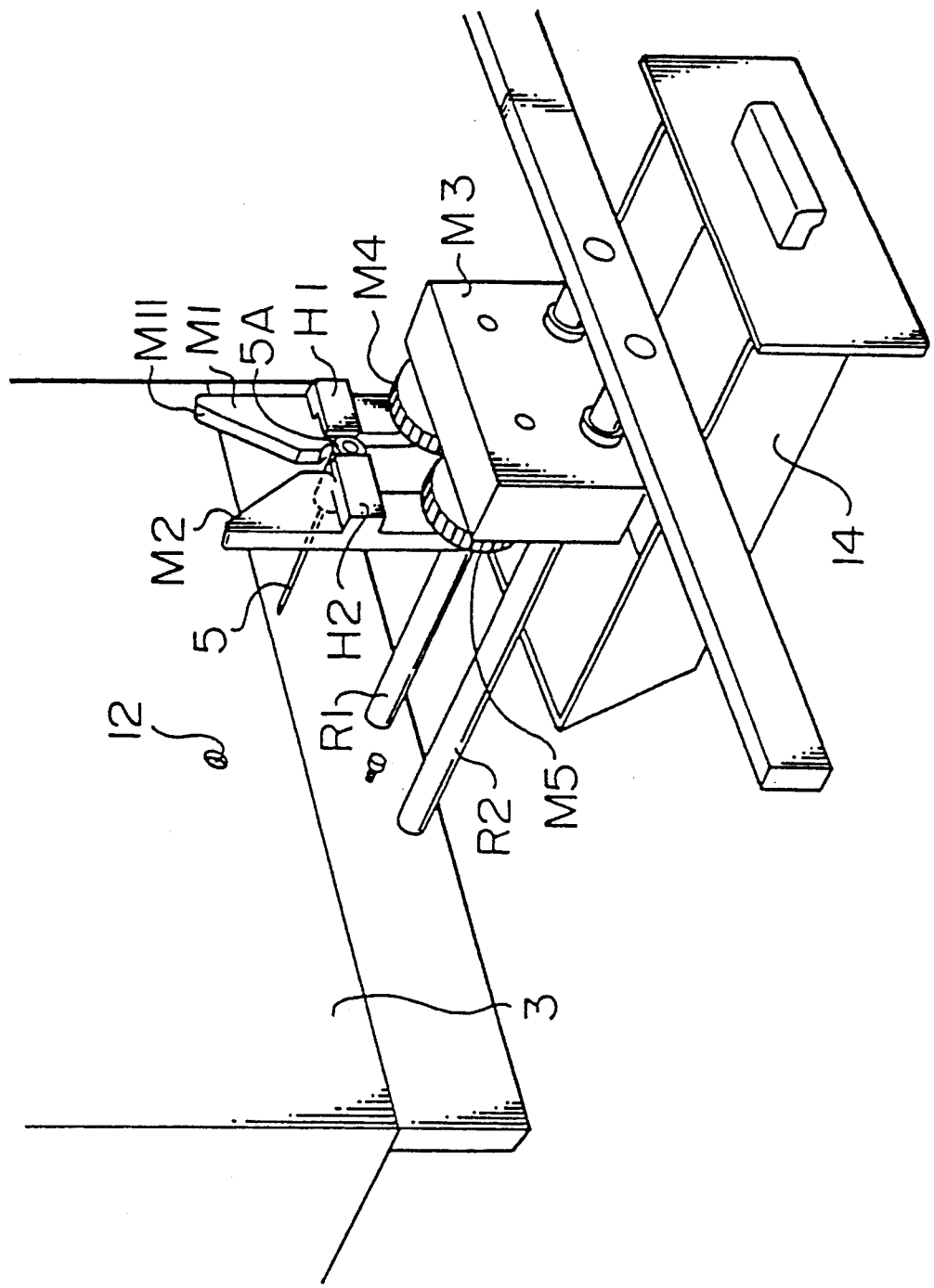

As shown in FIGS. 6 and 7, moving means has a pair of claws M1 and M2 for holding the sleeve 5A of the injection needle, and the claws M1 and M2 are rotatably mounted on a supporting member M3 and the claws M1 and M2 are fixed with a pair of gears M4 and M5 coupled with each other. There is provided a spring 9 between the claw M2 and the supporting member M3. Therefore, by inserting the injection needle 5 of an injection syringe 5B into the space between the upper portions of the claws M1 and M2, the sleeve 5A of the injection needle 5 slides the slanted surface portions M11 (FIG. 7) of the claws M1 and M2 and then the injection needle 5 is pinched by the claws M1 and M2 having the resilient force of the spring 9. Upon pulling the injection syringe 5B, the sleeve 5A of the injection needle 5 is stopped by a pair of projected plates H1 and H2 (FIG. 7) and therefore the injection needle 5 can be easily removed from the injection syringe 5B. The supporting member M3 for supporting the claws M1 and M2 is adapted to be slidable on a pair of rails R1 and R2 for guiding the supporting member M3. The supporting member M3 has an arm M6 one end of which is rotatably mounted on the supporting member M3. The other end of the arm M6 has an elongated hole M7 into which a pin M9 mounted at the periphery portion of a disk M8 is inserted. There is provided a spring 10 between the pin M9 and a pin M10 mounted on the arm M6. The disk M8 is rotated in the direction of arrow B by using a motor 11 thereby moving the supporting member M3 mounting the claws M1 and M2 holding the injection needle 5, along the rails R1 and R2 in the bi-direction of arrow C. The moving injection needle 5 can be inserted into a small hole 12 mounted on the front surface of the melting furnace 3 by the extent that the entire injection needle 5 has almost inserted. The injection needle 5 is molten for about 5-10 seconds, and the original formation of the injection needle 5 is no longer maintained, thereby forming a small ball (waste). The wasted needle is pulled from the small hole 12 backwardly passing through a restore position as shown in FIG. 2. A slanted portion 13A provided at the end point of a release member 13 is inserted into the space between the claws M1 and M2 against the resilient force of the spring 9 thereby releasing the injection needle 5 from the claws M1 and M2. As a result, the molten injection needle drops into a collection box 14. Then, the claws M1 and M2 are restored to the restore position as shown in FIG. 2.

According to the disposal apparatus mentioned above, the main switch SW1 of the disposal apparatus is actuated, and the injection needle 5 is held by the claws M1 and M2, and then a start switch SW2 is actuated. Then, the injection needle 5 is automatically molten in the melting furnace 3 for a short time, and then the injection needle 5 maintained by the claws M1 and M2 is pulled out from the melting furnace 3 and released by the releasing member thereby automatically dropping to the collecting box 14, under the control by a control device (not shown).

The present invention utilizing a plasma discharge with high temperature can be applied also to cut a metallic material, weld a metallic material such as plate or rod, and melt or weld ceramic materials such as porcelain or glass.

As mentioned above, according to the present invention a sharp end point of the injection needle is molten to deform to a ball-like formation with safety, and further it is completely sterilized due to the high temperature, as a result it can be dealt as it is just like a normal dust.

What is claimed is:

1. A melting disposal apparatus for injection needles comprising:
    means for generating electromagnetic microwaves, means for generating a plasma discharge with high temperatures by being irradiated with said electromagnetic microwaves, and moving means for grasping said injection needle and automatically inserting said injection needle into the zone in which said plasma discharge is produced and automatically retracting said injection needle from the zone in which said plasma discharge is produced and releasing said injection needle after said injection needle has been molten.

2. A melting disposal apparatus for injection needles according to claim 1, wherein said means for generating the plasma discharge with high temperature is composed of two tungsten wires disposed in such a manner that one end of each of said tungsten wires is disposed in adjacent to each other thereby producing said zone in which said plasma discharge is generated.

3. A melting disposal apparatus for injection needles according to claim 1, wherein the temperature generated by said means for generating a plasma discharge is within the range about 4000° C.-5000° C.

4. A melting disposal apparatus for injection needles according to claim 1 where said means for generating electromagnetic microwaves is a 100 volt, 500 watt generator which produces microwaves with a frequency of about 2450 KHz.

5. A melting disposal apparatus for injection needles according to claim 4 where said means for generating electromagnetic microwaves generates microwaves in intervals of from about five to about ten seconds.

6. A melting disposal apparatus for injection needles according to claim 1 where said moving means includes a pair of claws which are rotatably mounted on a supporting member.

7. A melting disposal apparatus for injection needles according to claim 6 where said claws are fixed with a pair of gears coupled to one another and at least one of said claws is spring biased in a closed position.

8. A melting disposal apparatus for injection needles according to claim 1 further including a collection box for said released, molten injection needle.

* * * * *